United States Patent [19]
Register et al.

[11] Patent Number: 5,881,928
[45] Date of Patent: Mar. 16, 1999

[54] DISPENSING GUN

[75] Inventors: John D. Register, N6709 370th, Menomonie, Wis. 54751; Mark O. Snyker, Oakdale, Minn.; Mike W. Horvath, Woodbury, Minn.; Thomas G. Skulley, St. Paul, Minn.

[73] Assignee: John D. Register, Menomonie, Wis.

[21] Appl. No.: 880,891

[22] Filed: Jun. 23, 1997

Related U.S. Application Data

[60] Provisional application No. 60/025,904, filed Sep. 9, 1996.

[51] Int. Cl.⁶ .................................................. B65D 88/54
[52] U.S. Cl. .......................... 222/340; 222/336; 222/386; 222/301
[58] Field of Search ..................................... 222/336, 340, 222/386, 79, 309, 43

[56] References Cited

U.S. PATENT DOCUMENTS

| | | |
|---|---|---|
| 3,606,085 | 9/1971 | Spilman . |
| 4,020,838 | 5/1977 | Phillips . |
| 4,033,346 | 7/1977 | Phillips . |
| 4,040,422 | 8/1977 | Kuhn . |
| 4,073,293 | 2/1978 | Phillips . |
| 4,245,757 | 1/1981 | Phillips . |
| 4,359,050 | 11/1982 | Reynolds ................................ 128/223 |
| 4,406,654 | 9/1983 | Bristow . |
| 4,425,121 | 1/1984 | Young . |
| 5,139,488 | 8/1992 | Klein ....................................... 604/184 |
| 5,154,324 | 10/1992 | Stratford . |
| 5,176,645 | 1/1993 | Guerrero . |
| 5,188,610 | 2/1993 | Rains . |
| 5,342,624 | 8/1994 | McNeill . |
| 5,662,244 | 9/1997 | Liu et al. ............................ 222/153.13 |

*Primary Examiner*—Andres Kashnikow
*Assistant Examiner*—Keats Quinalty
*Attorney, Agent, or Firm*—Palmatier, Sjoquist, Voigt & Christensen, P.A.

[57] ABSTRACT

A liquid dispensing gun having a dispensing limiter and a fill limiter which are utilized to regulate the volume of liquid dispensed to an animal. The liquid dispensing gun also includes an interchangeable cone and a shaft having a t-handle, a piston, a locking mechanism, and a plurality of positioning notches adapted for engagement to the dispensing limiter and fill limiter. A cylinder having a quick release end cap is engaged to the cone and a spring is positioned within the cylinder and engaged to the piston and to the cone for providing a spring assisted dispensing gun which minimizes the stress and/or fatigue to the hand and/or arm of a user. The dispensing gun is preferably adapted for use as a drench gun providing a user with the ability to utilize one hand on the dispensing gun and the free hand to control an animal during the introduction of drench to an animal.

23 Claims, 8 Drawing Sheets

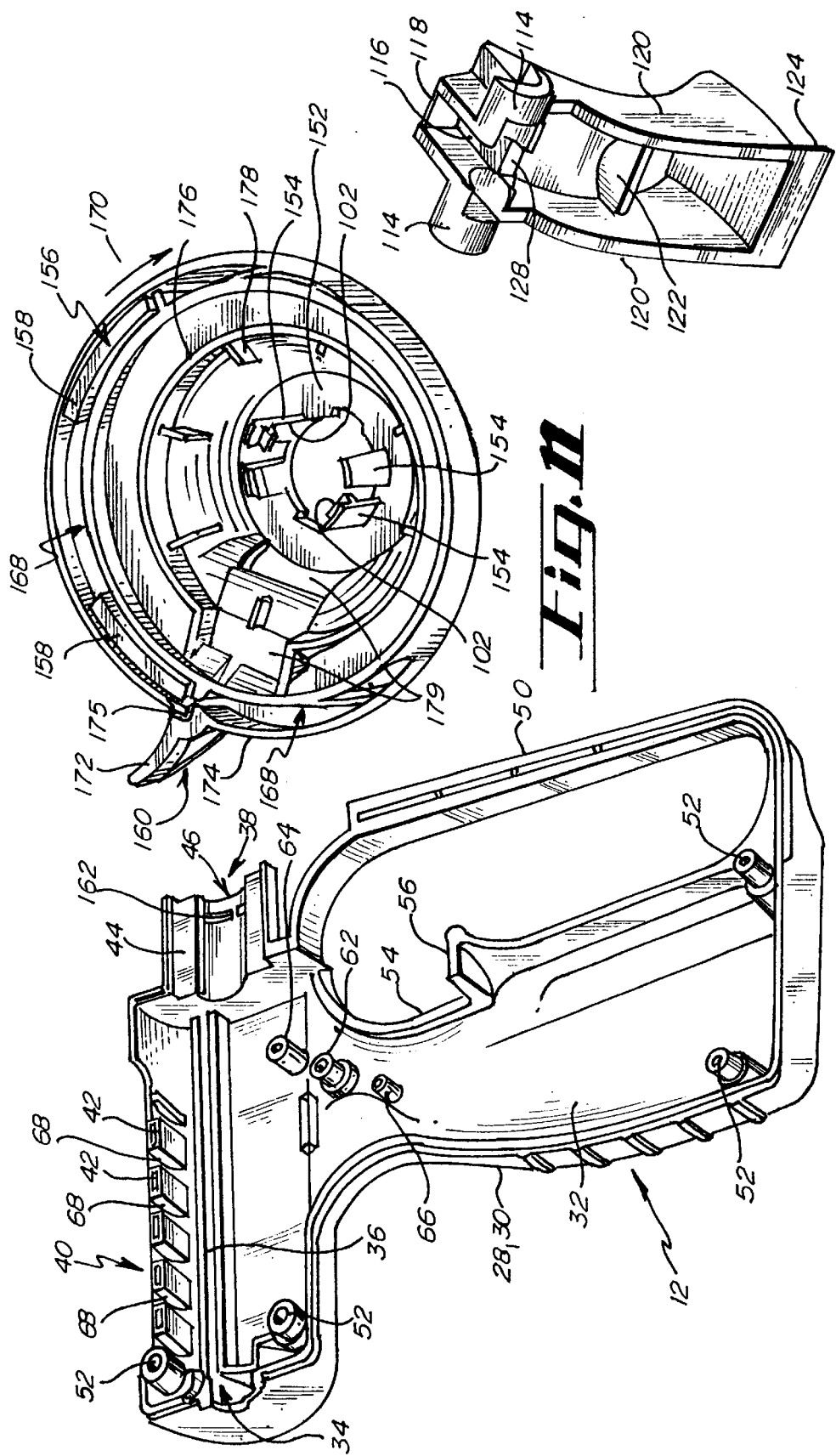

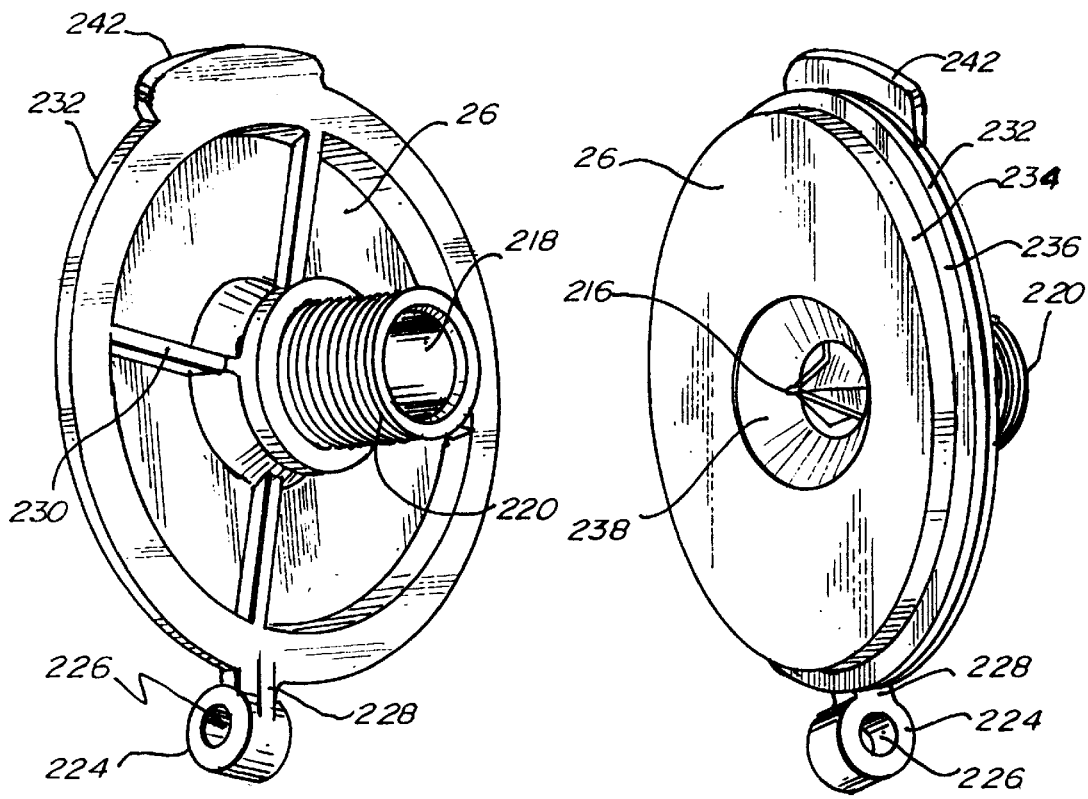
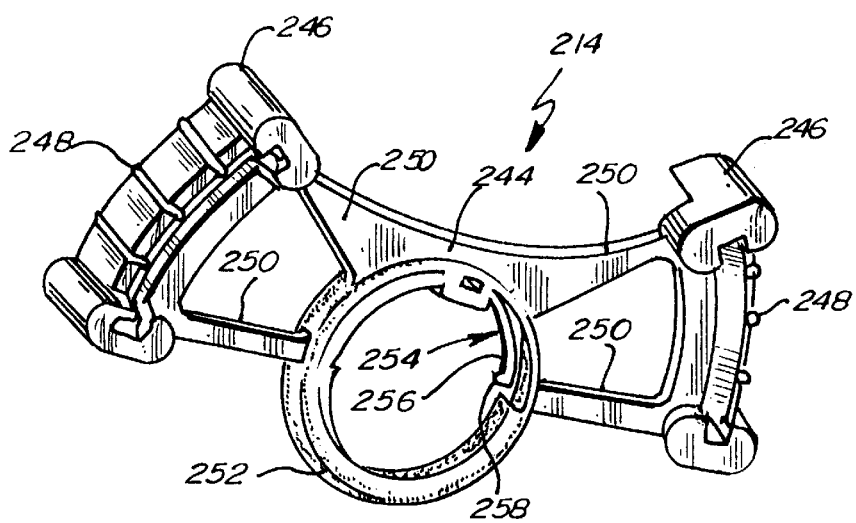

DISPENSING GUN

This application is derived from co-ending provisional patent application Ser. No. 60/025,904, filed Sep. 11, 1996, for a Dispensing Gun where the invention disclosed within this application has been invented by the same inventors as the co-pending provisional patent application Ser. No. 60/025,904 referenced-above.

BACKGROUND OF THE INVENTION

This invention relates to a dispensing gun and/or drench gun which may be utilized for providing drench or liquid to an animal such as cattle, sheep, and/or swine. In the past, drench or dispensing guns have failed to include a feature for enabling a user to regulate the rate of drench or liquid to be given to an animal. As such, animals frequently received the liquid and/or drench too rapidly leading to coughing and/or rejection of the liquid and the associated waste to a user. It is therefore desirable for a dispensing gun and/or drench gun to enable a user to deliver a desired volume of liquid to an animal in a regulated application to avoid and/or minimize the coughing and/or rejection by the animal, and the associated waste of the liquid and/or drench. The enclosed invention overcomes this drawback by enabling a user to regulate the rate of introduction of drench and/or liquid to an animal to fifty cubic centimeter increments, thereby minimizing loss or waste of drench.

In the past, dispensing and/or drench guns failed to include a means to assist in the dispensing of liquid and/or drench to minimize fatigue or stress to an individual. The use of the dispensing or drench guns as known frequently resulted in significant fatigue and/or pain to a user's hands and/or arms following the introduction of drench or liquid to a relatively few number of animals. The fatigue and stress experienced by a user then necessitated that the individual use two hands to squeeze the handle of the drench gun to dispense the drench. The user was thereby required to remove one hand from an animal which resulted in the corresponding loss of control during the dispensing or drenching process. It is therefore desirable for a dispensing gun to include a spring or means for expansion for assisting an individual to dispense liquid to minimize stress and/or fatigue to an individual's hand and/or arm. The present invention incorporates a spring or means for expansion which minimizes fatigue and/or stress to a user's hand and/or arm while simultaneously enabling a user to utilize the free hand to control the head of an animal to receive the liquid and/or drench.

In the past, drench or dispensing guns failed to provide flexibility with respect to the size of cylinders which contained different forms of drench such as vitamin supplements and/or medicine. As such, the utilization of the known drench guns was inconvenient when a different type or volume of liquid was to be dispensed to an animal. It is therefore desirable for a dispensing gun to include features which facilitate the convenient interchangeability of cylinders and/or cones which may be individually adjusted to satisfy size or other requirements of a particular type or dosage of drench for introduction to an animal.

In the past, drench or dispensing guns failed to provide a convenient mechanism for cleaning following a period of use. It is therefore desirable to provide a drench or dispensing gun which incorporates a cylinder having a pivotally connected end cap which may be easily retracted in order to facilitate cleaning.

In the past, drench or dispensing guns failed to provide an ergonomic shape which minimized stress and/or fatigue to the hand and/or arm of a user. It is therefore desirable to provide a drench or dispensing gun having an ergonomically designed grasping surface which minimizes stress and/or fatigue to a user during introduction of drench to an animal.

In the past, drench or dispensing guns failed to provide a convenient and easily grasped handle which was utilized to fill the dispensing gun with drench. It is very desirable to provide a drench and/or dispensing gun having a convenient t-handle shape which may be easily grasped and retracted by an individual for filling of a cylinder with drench to be dispensed to an animal.

SUMMARY

A liquid dispensing gun having a dispensing limiter and a fill limiter which are utilized to regulate the volume of liquid dispensed to an animal. The liquid dispensing gun also includes an interchangeable cone and a shaft having a t-handle, a piston, a locking mechanism, and a plurality of positioning notches adapted for engagement to the dispensing limiter and fill limiter. A cylinder having as quick release end cap is engaged to the cone and a spring is positioned within the cylinder and engaged to the piston and to the cone for providing a spring assisted dispensing gun which minimizes the stress and/or fatigue to the hand and/or arm of a user. The dispensing gun is preferably adapted for use as a drench gun providing a user with the ability to utilize one hand on the dispensing gun and the free hand to control an animal during the introduction of drench to an animal.

A principle object of the present invention is to provide a new and improved dispensing gun of relatively simple and inexpensive design and construction which fulfills the intended purpose of dispensing a liquid to be utilized as a drench for cattle without fear of damage to property and/or injury to cattle.

Another principle object of the present invention is to provide a spring assisted dispensing gun which minimizes stress and/or fatigue to the hand or arm of an individual during use.

Still another principle object of the present invention is to provide a dispensing gun which is flexible to accommodate multiple or single dose applications of a predetermined volume.

Still another principle object of the present invention is to provide a dispensing gun which may be easily cleaned by an individual.

Still another principle object of the present invention is to provide a dispensing gun which is flexible to receive an individual bladder or cartridge of liquid to be dispensed.

Still another principle object of the present invention is to provide a dispensing gun which minimizes dripping or loss of liquid during periods of non-use.

Still another principle object of the present invention is to provide a dispensing gun which is flexible to enable substitution of cones and/or cylinders to accommodate various applications as desired by an individual such as for drench, medicine, food, and/or lubrication.

Still another principle object of the present invention is to provide a dispensing gun having an ergonomic shape for maximization of comfort to an individual during use.

Still another object of the present invention is to provide a dispensing gun which is preferably adapted for one-handed use by an individual.

Still another principle object of the present invention is to provide a dispensing gun having an increased capacity to dispense a volume of liquid in excess of three hundred cubic centimeters.

Still another principle object of the present invention is to provide a dispensing gun having flexibility to repeatedly dispense liquid in fifty cubic centimeter increments.

Still another principle object of the present invention is to provide a dispensing gun having flexibility to accommodate various tube lengths for dispensing liquid to different breeds of animals.

Still another principle object of the present invention is to provide a multiple use dispensing gun which is durable for use over an extended period of time by an individual.

A feature of the present invention includes a dispensing gun having a dispensing limiter which may be utilized to dispense a desired volume of liquid in a single application or in fifty cubic centimeter increments as preferred by an individual.

Another feature of the present invention includes a dispensing gun having an internal spring which is adapted to engage a piston for assisting the dispensing of a liquid, thereby minimizing stress and/or fatigue to the hand and/or arm of an individual.

Still another feature of the present invention includes a dispensing gun having an end cap which may be conveniently disengaged from a cylinder to facilitate substitution of a different sized cylinder.

Still another feature of the present invention includes a fill limiter which is adapted to engage a shaft having a piston where the fill limiter is utilized to regulate the total volume of liquid to be dispensed through the dispensing gun.

Still another feature of the present invention is a dispensing limiter which is adapted to engage notches integral to the shaft for dispensing liquid in fifty cubic centimeter increments.

Still another feature of the present invention is a shaft having a t-handle which assists an individual in filling the cylinder of the dispensing gun with a desired volume of liquid.

Still another feature of the present invention is the provision of a cone which is engaged to the handle of the dispensing gun which may be easily replaced to accommodate use of various sized cylinders for dispensing liquid.

Still another feature of the present invention is the provision of an exchangeable compression spring for engagement to the cone and to the piston for assisting in the dispensing of liquid from the dispensing gun.

Still another feature of the present invention is the provision of a quick release piston which may be easily removed from the shaft to facilitate substitution and/or cleaning.

Still another feature of the present invention is an end cap which is adapted to pivotally engage the cylinder of the dispensing gun to facilitate cleaning.

Still another feature of the present invention is an end cap which is integral to a cylinder of the dispensing gun which may be easily replaced to facilitate use with varying applications.

Still another feature of the present invention is an end cap which is adapted to releasably couple and accommodate the use of varying length application nozzle hoses.

Still another feature of the present invention is the provision of a loop handle and finger guard for maximization of ergonomic comfort and safety of the dispensing gun to an individual during use.

Still another feature of the present invention is the provision of a break-open cylinder which may accommodate the use of a bladder or cartridge enclosing a desired volume of liquid for facilitation of the removal, interchangeability, or cleaning of the cylinder and/or shaft and piston.

BRIEF DESCRIPTION OF THE DRAWINGS

FIG. 9 is an isometric detail view of the first handle 28;

FIG. 10 is a rear detail isometric view of the dispensing limiter;

FIG. 11 is a detail isometric rear view of the cone;

FIG. 14 is a detail front isometric view of the end cap;

FIG. 15 is a detail isometric rear view of the end cap;

FIG. 16 is a detail isometric front view of the retainer;

DETAILED SPECIFICATION OF THE PREFERRED EMBODIMENT

Figure 1:
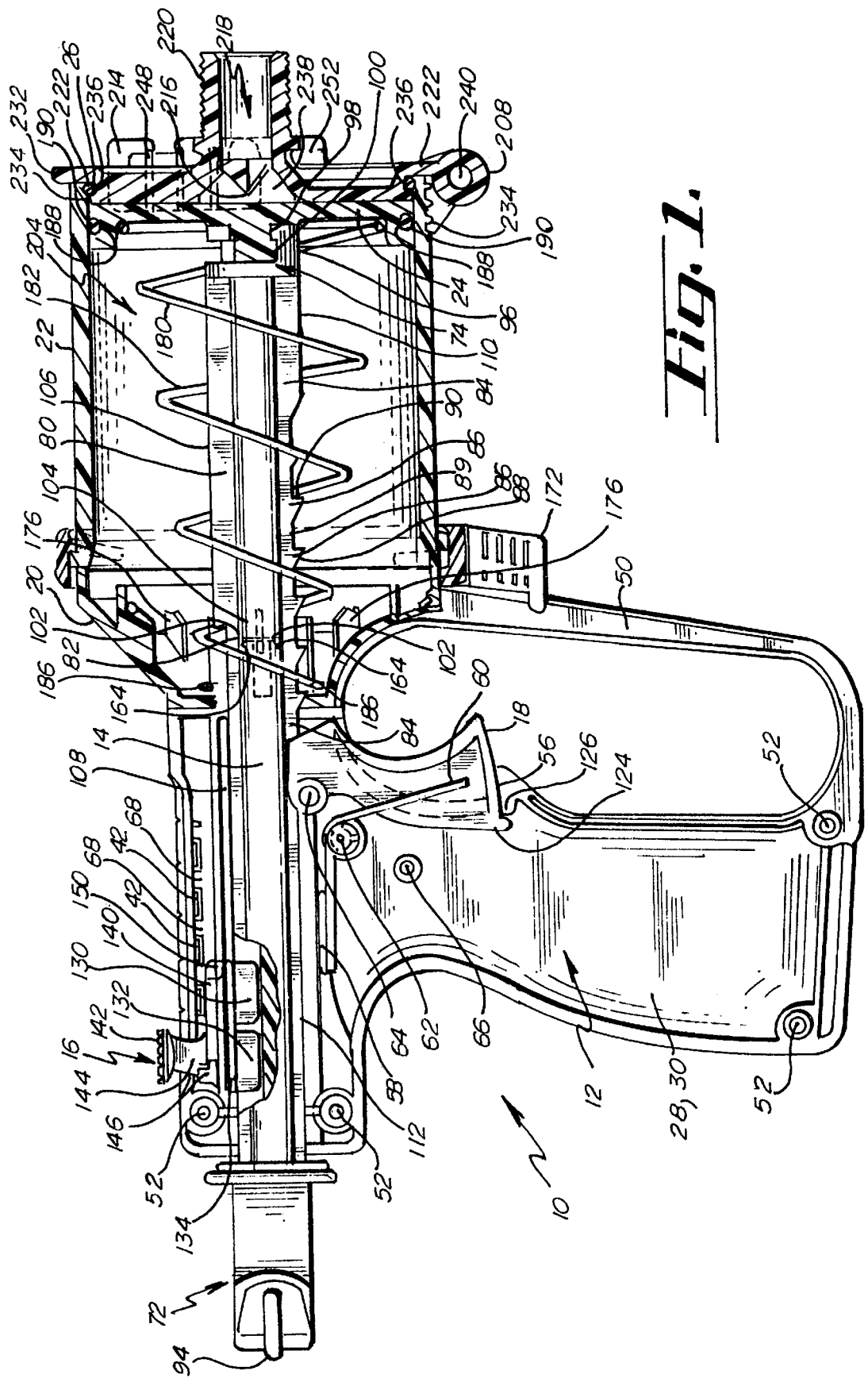
FIG. 1 is a cross-sectional side view of the dispensing gun.

One form of the dispensing gun is illustrated and described herein. The dispensing gun is referred to in general by the numeral 10. The dispensing gun 10 in general includes a handle 12, a shaft 14, a fill limiter 16, a dispensing limiter 18, a cone 20, a cylinder 22, a piston 24, and an end cap 26. (FIG. 1)

The handle 12 may preferably be formed of a first handle member 28 and a second handle member 30. The first handle member 28 and the second handle member 30 are preferably mirror images of each other and may be positioned in confronting relationship to each other to define an internal cavity 32. (FIG. 9)

An arcuate rear aperture 34 preferably traverses both the first and second handle members 28, 30 respectively. A positioning channel 36 preferably extends horizontally forward from a location adjacent to the rear aperture 34 to a position proximate to the nose 38 on each of the first and second handle members 28, 30 respectively. The positioning channels 36 preferably receive and define a course of forward and/or rearward movement for the fill limiter 16 during use of the dispensing gun 10. A positioning groove 40 also preferably extends and traverses the top of each of the first and second handle members 28, 30 respectively. The positioning grooves 40 preferably enable the fill limiter 16 to extend above the first and second handle members 28, 30 respectively. The fill limiter 16 may then be manipulated by an individual into a desired position. (FIGS. 1 and 9)

Adjacent to the positioning groove 40 within the internal cavity 32 are located a plurality of regularly spaced and aligned positioning stops 42 for each of the first and second handle members 28, 30 respectively. The positioning stops 42 are preferably spaced at intervals corresponding to fifty cubic centimeter increments to permit the fill limiter 16 to be shifted/manipulated into a desired location during filling of the dispensing gun 10 with liquid and/or drench. (FIGS. 1 and 9)

Each of the first and second handle members 28, 30 respectively includes a nose portion 44 which includes a semi-circular nose aperture 46 and nose slots 162. The nose portion 44 is preferably adapted for penetrating engagement within the cone 20 for releasable affixation thereto. The nose portion 44 may be releasably engaged to the cone 20 through engagement of the finger tabs 102 of the cone 20 within the nose slots 162. (FIGS. 1, 9, 11 and 12)

Each of the first and second handle members 28, 30 respectively may also be ergonomically shaped and may include a plurality of finger grooves at the discretion of an individual. It should also be noted that each of the first and second handles 28, 30 respectively may also include an arcuate finger guard 50 which may be utilized to protect the fingers and the hand of an individual during use of the dispensing gun 10.

Each of the first and second handle members 28, 30 respectively may include a plurality of screw tabs 52 which are preferably adapted for nesting engagement with screw recesses (not shown) whereupon screws may be utilized to releasably attach the first handle member 28 to the second handle member 30. (FIG. 9)

Each of the first and second handle members 28, 30 respectively may also include a dispensing limiter channel 54, and a dispensing limiter ledge 56. The dispensing limiter channels 54 and dispensing limiter ledges 56 are adapted to receive the dispensing limiter 18 for positioning in a convenient location for use by an individual. (FIGS. 1 and 9)

Within the internal cavity 32 of each of the first and second handle members 28, 30 respectively is located a dispensing spring ledge 58 which is adapted for engagement to a dispensing spring 60. A dispensing spring pin 62 may also be positioned within the internal cavity 32 where the dispensing spring pin 62 is adapted for fixed positioning of the dispensing spring 60 relative to the first and second handle members 28, 30 respectively and to the dispensing limiter 18. The dispensing limiter 18 may also be positioned within the internal cavity 32, where the dispensing limiter pivot pin 64 is preferably adapted to engage the dispensing limiter 18 providing for pivotal rotation of the dispenser limiter 18 with respect to the first and second handle members 28, 30 respectively as within the dispensing limiter channel 54 during use of the dispensing gun 10. (FIGS. 1 and 9)

A dispensing limiter stop 66 may also be positioned within the internal cavity 32 for each of the first and second handle members 28, 30 respectively for limiting the rearward rotation of the dispensing limiter 18 with respect to the first and second handle members 28, 30 respectively during use of the dispensing gun 10. (FIGS. 1 and 9)

It should be noted that the dispensing spring 60 may be of a torsion or coiled type, or of a flat type, at the discretion of an individual.

The positioning stops 42 are preferably regularly spaced within the interior of the first and second handle members 28, 30 along the length of the positioning groove 40, and are placed perpendicular to the positioning groove 40, to define a plurality of locking channels 68. It should be noted that the regular spacing between the locking channels 68 permits a user to fill the dispensing gun 10 with liquid at fifty cubic centimeter increments, where the dispensing gun 10 has the flexibility to hold a volume of liquid varying between fifty cubic centimeters and three hundred cubic centimeters at the discretion of an individual. (FIGS. 1 and 9)

The nose portions 44 preferably extend forwardly from the first and second handle members 28, 30 respectively and are adapted for penetrating engagement into the cone 20. The nose portions 44 preferably include nose slots 162 which may be used to engage the finger tabs 102 to affix the cone 20 to the first and second handle members 28, 30 respectively. Alternatively, a nose collar 104 may be utilized to affix the cone 20 to the first and second handle members 28, 30 respectively. It should be noted that the cone 20 assists in the affixation of the first handle member 28 to the second handle member 30 through the engagement, and the releasable attachment of, the respective nose portions 44 together. (FIGS. 1, 9, 11 and 12)

The rear aperture 34 and the nose aperture 46 are preferably adapted for slidable and receiving engagement of the shaft 14. The shaft 14 may be adjustably positioned through the rear aperture 34 and the nose aperture 46 during use of the dispensing gun 10. (FIG. 1)

It should be noted that the handle 12 may be formed of any material as is desired by an individual including the use of plastics or metals which may include finger grooves and a non-slip palm surface in order to facilitate convenience during use. It should also be noted that the size dimensions for the handle 12 may vary considerably dependent upon the hand size of an individual user.

The shaft 14 is preferably forwardly and rearwardly adjustable within the internal cavity 32 relative to the handle 12, cone 20, and cylinder 22. (FIG. 1)

Figure 2:
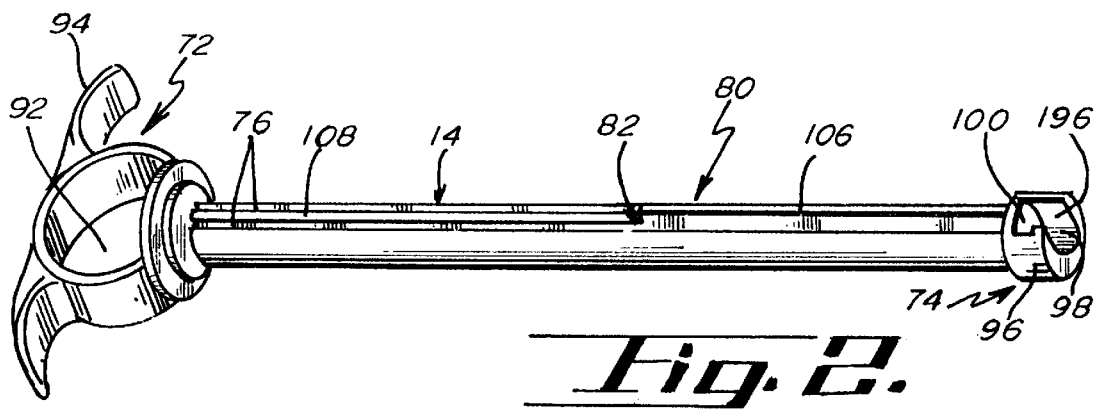
FIG. 2 is a detailed isometric view of the shaft.
Figure 3:
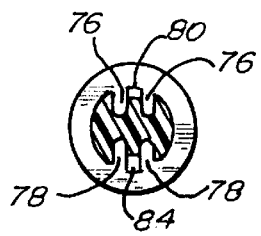
FIG. 3 is a cross-sectional end view of the shaft taken along the line of 3—3 of FIG. 2.
Figure 4:
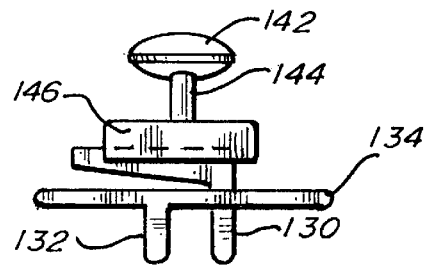
FIG. 4 is a detail end view of the fill limiter.
Figure 5:
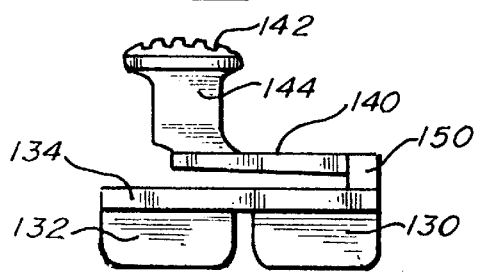
FIG. 5 is a detail side view of the fill limiter.
Figure 6:
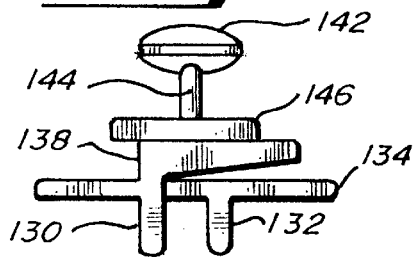
FIG. 6 is a detail opposite end view of the fill limiter.
Figure 7:
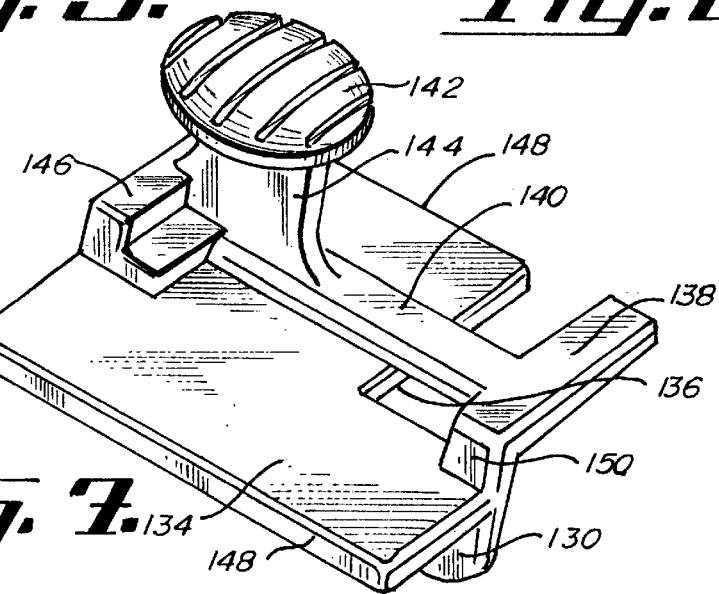
FIG. 7 is a detail isometric view of the fill limiter.
Figure 8:
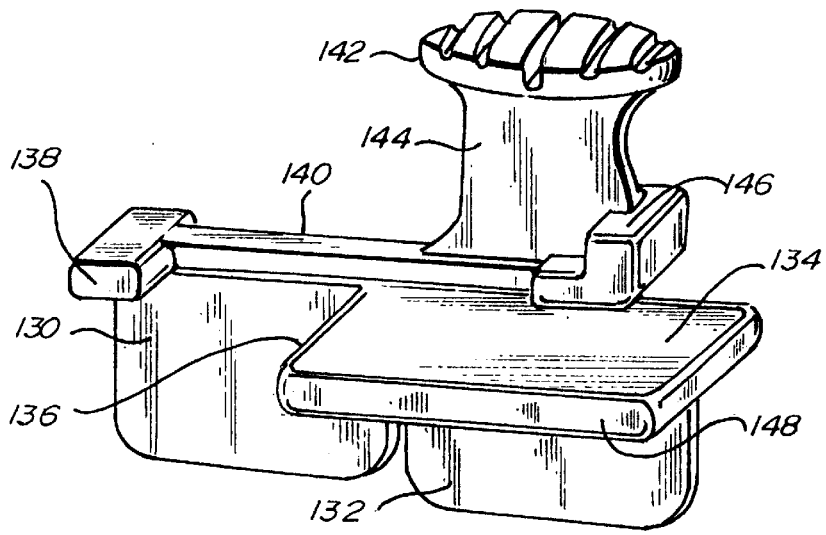
FIG. 8 is an alternative isometric detail view of the fill limiter.

The shaft 14 is preferably elongate having a grasping end referred to in general by the numeral 72 and a piston end referred to in general by the numeral 74. The elongate shaft 14 may also include a pair of first parallel channels 76 and a pair of second parallel channels 78. The pair of first parallel channels 76 and pair of second parallel channels 78 generally extend from the grasping end 72 to the piston end 74. The pair of first parallel channels 76 define a first ridge 80 which preferably includes a vertical ledge 82 which is positioned approximately equal distances between the grasping end 72 and the piston end 74. Alternatively, the vertical ledge 82 may be positioned at any preferred location between the grasping end 72 and the piston end 74, at the discretion of an individual, in order to facilitate the filling of the dispensing gun 10 with a desired volume of liquid. The pair of second parallel channels 78 preferably define a second ridge 84 which preferably includes a plurality of notches 86 or teeth. The plurality of notches 86 or teeth preferably extend approximately one-half the length of the second ridge 84 extending from a position proximate to the mid-point between the grasping end 72 and the piston end 74 extending forwardly toward the piston end 74. It should be noted that the plurality of notches 86 or teeth each contain an angular portion 88 and a vertical portion 90 where the angled portion 88 preferably extends rearwardly toward the grasping end 72. (FIGS. 2 and 3)

The grasping end 72 is preferably t-shaped having a centrally positioned ring 92 and a pair of grasping surfaces 94 extending outwardly therefrom. It should be noted that the ring 92 and grasping surfaces 94 are preferably positioned perpendicular to the first and second ridges 80, 84 respectively. The grasping surfaces 94 are preferably adapted to engage an individual's hand during the rearward retraction of the shaft 14 during the filling of the cylinder 22 with liquid to be dispensed to an animal through use of the dispensing gun 10. (FIGS. 2 and 3)

Figure 23:
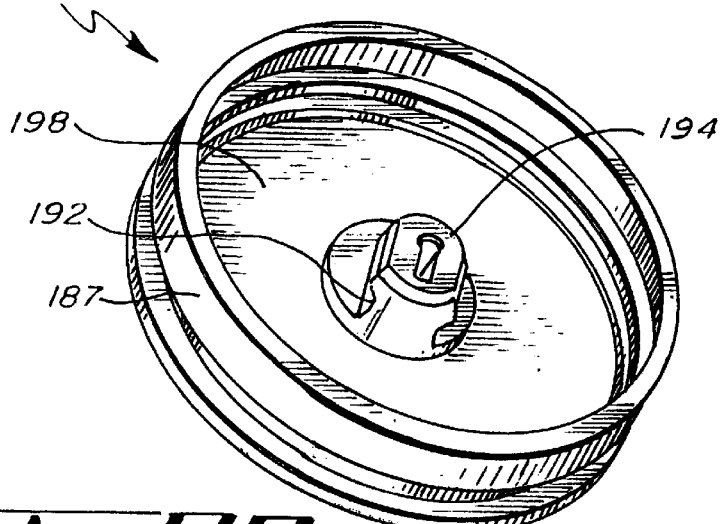
FIG. 23 is an isometric alternative view of the piston.

The piston end 74 generally includes a collar portion 96 having a piston receiving slot 98 and a piston affixation notch 100. The piston receiving slot 98 and piston affixation notch 100 are preferably adapted to conveniently and quickly receive and engage a piston 24 for releasable affixation to the shaft 14 during assembly of the dispensing gun 10. The piston receiving slot 98 and piston affixation notch 100 preferably provide flexibility to enable replacement of the piston 24 for a piston 24 of another size as desired by an individual for use with a desired size cylinder 22. The piston receiving slot 98 may be of any preferred shape as desired by an individual, and may be key-hole shaped, for engagement to a piston 24 as depicted in FIG. 23 for provision of additional structural strength and integrity of the piston end 74. It should be noted that an individual may desire that the piston 24 be permanently attached to the shaft 14 or may desire utilization of alternative affixation mechanisms or a locking means to secure the piston 24 to the shaft 14. (FIGS. 1, 2, 3 and 18)

The pair of first parallel channels 76 preferably extend along the upper length of the shaft 14 defining a first ridge 80. The first ridge 80 preferably extends upwardly from the shaft 14. The first ridge 80 may include an elevated portion 106 and a lower portion 108. The vertical ledge 82 preferably extends between the elevated portion 106 and the lower portion 108. The vertical ledge 82 is preferably adapted to engage the fill limiter 16 functioning as a stop to restrict the volume of liquid to be disposed within the cylinder 22 of the dispensing gun 10. Alternatively, a stop may extend from the shaft 14 for engagement to the fill limiter 16 to regulate the volume of liquid to be disposed within the cylinder 22 during use of the dispensing gun 10. (FIGS. 1, 2 and 3)

The pair of second parallel channels 78 also preferably extend along the lower length of the shaft 14 defining a second ridge 84 which preferably extends downwardly from the shaft 14. The second ridge 84 may also include a heightened portion 110 and a reduced portion 112. The plurality of notches 86 or teeth preferably provide for the transition between the heightened portion 110 and the reduced portion 112 of the second ridge 84. Each of the plurality of notches 86 preferably include an angular portion 88 and a vertical portion 90. The plurality of notches 86 are preferably spaced along the shaft 14 to permit the application/discharge of liquid and/or drench in fifty cubic centimeter increments during use of the dispensing gun 10. (FIGS. 1, 2 and 3)

The plurality of notches 86 are preferably adapted for engagement to the dispensing limiter 18 to regulate the volume of liquid to be dispensed to an animal during utilization of the dispensing gun 10. The angular portions 84 of the plurality of notches 86 preferably extend or angle rearwardly toward the grasping end 72 of the shaft 14. The plurality of notches 86 are preferably located along the second ridge 84 forwardly from the mid-point of the shaft 14 being regularly spaced toward the piston end 74. (FIGS. 1, 2, 3 and 10)

The angle portions 88 of the plurality of notches 86 are preferably adapted to facilitate the rearward retraction of the shaft 14 past the dispensing limiter 18 during the filling of the dispensing gun 10 with drench and/or liquid. The vertical portions 90 of the plurality of notches 86 preferably engage the dispensing limiter 18 during use of the dispensing gun 10 to regulate the rate and/or volume of drench or liquid to be dispensed to an animal. (FIGS. 1, 2, 3 and 10)

The shaft 14 is preferably positioned within the internal cavity 32 prior to the affixation of the first and second handle members 28, 30 to each other. The shaft 14 preferably is positioned within the rear aperture 34 where the grasping end 72 is positioned to the rearward exterior of the handle 12. The shaft 14 also is positioned within the nose aperture 46 where the piston end 74 is preferably positioned forwardly and exterior to the handle 12. (FIGS. 1 and 9)

An individual may clasp the ring 92 and grasping surfaces 94 to rearwardly retract the shaft 14, which in turn, through vacuum suction, enables the cylinder 22 to be filled with a desired volume from a common bulk container of liquid and/or drench in a single step. In addition, the shaft 14, via the plurality of notches 86, enables the dispensing gun 10 to regulate, via the dispensing limiter 18, the volume of drench and/or liquid to be introduced to an animal to fifty cubic centimeter increments. Further, the shaft 14, via the vertical ledge 82, enables an individual to regulate the volume of liquid and/or drench to be disposed within the cylinder 22 through selection and positioning of the fill limiter 16. The cylinder 22 of the dispensing gun 10 may thereby be filled with drench and/or liquid having a volume varying between fifty and three hundred fifty cubic centimeters. (FIG. 1)

The dispensing limiter 18 includes an arcuate positioning tab 114 which is adapted to engage and permit pivotal rotational movement of the dispensing limiter 18 about the dispensing limiter pivot pins 64. The dispensing limiter 18 also includes a dispensing channel 116 which includes a sufficient length dimension to enable the downward rotation of the dispensing limiter 18 about the dispensing limiter pivot pins 64 to enable the forward sliding movement of the shaft 14. The length dimension for the dispensing channel 116 preferably provides the plurality of notches 86 with sufficient clearance to not engage the dispensing barrier stop 118 during retraction of the dispensing limiter 18. The dispensing barrier stop 118 preferably traverses the dispensing channel 116. The dispensing barrier stop 118 is preferably adapted to engage the vertical portions 90 of the plurality of notches 86 to limit and restrict the forward motion of the shaft 14 during the regulation of drench and/or liquid to be applied to an animal. (FIGS. 1 and 10)

The dispensing limiter 18 preferably includes a pair of dispensing sidewalls 120 which are adapted for placement within the dispensing limiter channels 54 and dispensing limiter ledges 56. A support member 122 preferably traverses between the pair of dispensing sidewalls 120. The support member 122 is preferably adapted for engagement to the dispensing spring 60. The dispensing limiter 18 also includes a rotational stop 124 which is adapted to engage the internal rearward edge 126 of the dispensing limiter ledge 56 to prevent forward rotation of the dispensing limiter 18 about the dispensing limiter pivot pin 64, beyond the handle 12. The dispensing limiter 18 also includes a spring channel 128 which is preferably adapted to assist in the retention of the dispensing spring 60 in a desired location with respect to the dispensing limiter 18 during use. (FIGS. 1 and 10)

In operation, the dispensing limiter 18 is in a forward position where the rotational stop 124 is in contact with the internal rearward edge 126 of the dispensing limiter ledge 56. (FIGS. 1 and 10)

An individual may then squeeze the dispensing limiter 18 which rotates the pair of dispensing sidewalls 120 rearwardly within the internal cavity 32 compressing the dispensing spring 60, which simultaneously causes rotation of the arcuate positioning tabs 114 about the dispensing limiter pivot pin 64. The length of the dispensing channel 116, and the position of the arcuate positioning tabs 114 rearwardly of the dispensing barrier stop 118 and dispensing limiter pivot pin 64, causes the dispensing barrier stop 118 to rotate downwardly, disengaging the dispensing barrier stop 118 from the vertical portion 90 of one of the plurality of notches 86. The means for expansion may then uncoil or expand, assisting in the movement of the shaft 14 forwardly to assist in the introduction of drench to an animal. (FIGS. 1 and 10)

In order to regulate the dispensing of drench to fifty cubic centimeter increments, an individual may immediately release the dispensing limiter 18 following an initial squeezing or manipulation. The release of the dispensing limiter 18 permits dispensing spring 60 to expand against the support member 112 rotating the pair of dispensing sidewalls 120 forwardly for engagement of the rotational stop 124 to the internal rearward edge 126. Simultaneously, the dispensing barrier stop 118 will rotate upwardly to engage the angled portion 88, spacer portion 89, or next available vertical portion 90 of the next available notch 86, as the shaft 14 moves forwardly toward the nose 38. The engagement between the dispensing barrier stop 118 and the next available vertical portion 90 terminates the forward movement of the shaft 14, thereby terminating further expulsion of drench and/or liquid from the dispensing gun 10. (FIGS. 1 and 10)

Alternatively, to dispense a volume of drench and/or liquid in excess of fifty cubic centimeters, an individual need only continue to retract or depress the dispensing limiter 18 whereon the means for expansion will assist in automatically moving the shaft 14 forwardly to apply an entire desired volume of liquid and/or drench to an animal. It should be noted that the squeezing of the dispensing limiter 18, combined with the means for expansion, will preferably result in the introduction of the entire contents of the cylinder 22 to an animal. If an individual desires to terminate the introduction of drench and/or liquid to an animal, then the individual may conveniently release the dispensing limiter 18 at any time to terminate further dispensing of drench and/or liquid. It should also be noted that the rearward rotation of the dispensing limiter 18 within the internal cavity 32, is restricted by the dispensing limiter stop 66 which prevents manipulation of the pair of dispensing sidewalls 20 completely within the internal cavity 32, thereby eliminating the possibility of undesirable sticking or jamming of the dispensing limiter 18 with respect to the handle 12. (FIGS. I and 10)

It should also be noted that the angled portions 88 of the notches 86 assist in the filling of the cylinder 22 with drench and/or liquid. During filling of the cylinder 22, the grasping end 72 of the shaft 14 is retracted rearwardly with respect to the handle 12. The dispensing limiter 18 is then in the forward position where the rotational stop 124 is engaged to the internal rearward edge 126 of the dispensing limiter ledge 56. The engagement between the angled portions 88 and the dispensing barrier stop 118 will preferably cause the dispensing limiter 18 to rotate rearwardly and downwardly about the dispensing limiter pivot pins 64 in order to permit the shaft 14 and plurality of notches 86 to pass the dispensing barrier stop 118. The retraction of the shaft 14 may then continue until such time as the cylinder 22 is filled with a desired volume of liquid and/or drench. It should be noted that as each of the plurality of angled portions 88 of the notches 86 traverse the dispensing barrier stop 118, the dispensing limiter 18 will rotate slightly inwardly into the Internal cavity 32 to permit the passage of each individual notch 86. Upon the passing of an individual notch 86, the dispensing limiter 18 will automatically rotate forwardly via the expansion of the dispensing limiter spring 60 until such time as engagement with the next angled portion 88 occurs. (FIGS. 1 and 10)

The fill limiter 16 may engage or straddle the first ridge 80 and slidably engage the pair of first parallel channels 76 of the shaft 14. The fill limiter 16 may also engage to the positioning channels 36 of the first and second handle members 28, 30 respectively. The fill limiter 16 is also preferably adapted for slidable positioning within the positioning groove 40 and is further adapted for fixed adjustable positioning with respect to the positioning stops 42. (FIGS. 2, 3, 4, 5, 6, 7 and 8)

Figure 8A:
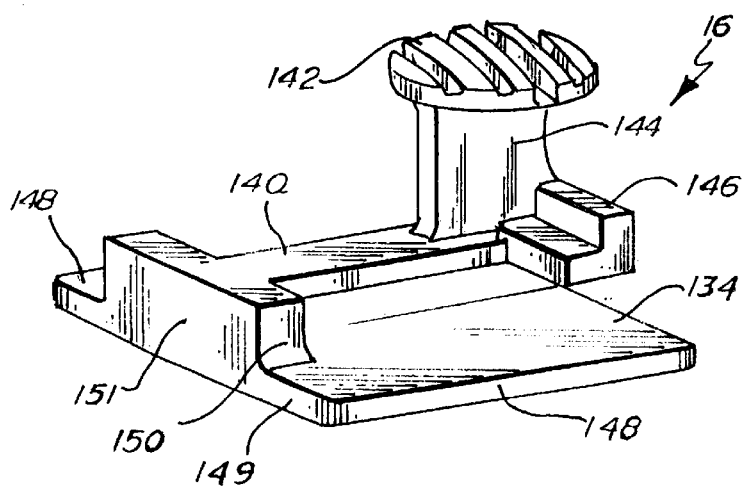
FIG. 8a is an alternative isometric detail view of the fill limiter.

The fill limiter 16 may include a first keel 130 which may be rearwardly staggered with respect to and laterally spaced or offset from a second keel 132. The first and second keels 130, 132 respectively depend from a horizontal base 134. The first and second keels 130, 132 are preferably adapted to straddle the lower portion 108 of the first ridge 80 and are preferably slidably positioned within the pair of first parallel channels 76 of the shaft 14. The pair of first parallel channels 76 preferably serve as tracks for the first and second keels 130, 132 respectively, providing a set path of forward and rearward motion for the fill limiter 16 with respect to the shaft 14, positioning groove 40, and handle 12. The first and second keels 130, 132 thereby preferably function to adjustably position the fill limiter 16 in an exact desired location with respect to the shaft 14 and the positioning stops 42. (FIGS. 2, 3, 4, 5, 6, 7 and 8) Alternatively, the exterior edges 148 of the horizontal base 134 are preferably slidably engaged within the positioning channels 36. The positioning channels 36, in this embodiment, preferably serve as tracks for the fill limiter 16, providing a set path of forward and rearward motion for the fill limiter 16 with respect to the shaft 14, positioning groove 40, and handle 12. It should be noted that in this embodiment, the first and second keels 130, 132 are not necessary to the functioning of the fill limiter 16 as engaged to the positioning stops 42 and/or the locking channels 68. It should also be noted that in this embodiment that the fill limiter 16 is positioned above the shaft 14 and is not engaged thereto, where the fill limiter 16 functions as a stop during the filling of the dispensing gun 10 with a desired volume of liquid. (FIG. 8a)

The horizontal base 134 preferably includes a pair of exterior edges 148. The horizontal base 134 also preferably includes a cutaway portion which defines a stop ledge 136. The stop ledge 136 preferably extends from one exterior edge 148 of the horizontal base 134 inwardly to approximately a mid-point location between the two exterior edges 148. The exterior edges 148 are preferably adapted for slidable engagement within the positioning channels 36 of the first and second handle members 28, 30 respectively. The stop ledge 136 is preferably adapted for engagement to the vertical ledge 82 to limit the rearward retraction of the shaft 14 during filling of the cylinder 22 with drench and/or liquid. (FIGS. 2, 3, 4, 5, 6, 7 and 8) In an alternative embodiment, as depicted in FIG. 8a, the fill limiter 16 does not include a cutaway portion defining a stop ledge 136. In this embodiment, the horizontal base 134 is a structurally sturdy integral one-piece unit having a rearward edge 149 and a rearward surface 151 extending vertically upward from the rearward edge 149. The rearward surface 151 may preferably be centered between the exterior edges 148. In this embodiment, the rearward edge 149 and/or the rearward surface 151 preferably function as a stop. The rearward edge 149 and/or the rearward surface 151 are preferably adapted for engagement to the vertical ledge 82 of the shaft 14 to limit the rearward retraction of the shaft 14 during the filling of the cylinder 22 with drench and/or liquid during use of the dispensing gun 10. (FIG. 8a) In this embodiment, it should be noted that the positioning locks 146 engage the positioning stops 42 and/or the locking channel 68 in an identical manner as described herein for the earlier described embodiments. (FIG. 8a)

A lateral support bar 138 preferably extends horizontally and outwardly from a vertical support bar post 150 above the cutaway portion and forwardly to the stop ledge 136. A longitudinal extension bar 140 preferably extends perpendicularly rearward from the lateral support bar 138 above the horizontal base 134. A vertical support member 144 preferably extends upwardly from the longitudinal extension bar 140 opposite to the lateral support bar 138. A manipulation tab 142 is preferably engaged to the vertical support member 144. The vertical support member 144 preferably contains a sufficient length dimension to place the manipulation tab 142 above the positioning groove 40 to the exterior of the upper portion of the handle 12. (FIGS. 2, 3, 4, 5, 6, 7 and 8)

A positioning lock 146 preferably extends perpendicularly outward and upward from the rear edge of the longitudinal extension bar 140. The positioning lock 146 preferably has a sufficient width dimension to traverse the positioning groove 40 of each of the first and second handle members 28, 30 respectively and is adapted for engagement within a pair of aligned and regularly spaced locking channels 68. (FIGS. 2, 3, 4, 5, 6, 7 and 8)

The vertical dimension for the support bar post 150 provides a torsion-like affect between the manipulation tab 142 and the horizontal base 134. The natural position for the longitudinal extension bar 140 is therefore parallel to the horizontal base 134. When the longitudinal extension bar 140 is parallel to the horizontal base 134, the positioning locks 146 are aligned to, and positioned within, a pair of locking channels 68. One of the aligned pair of locking channels 68 is preferably positioned on each side of the vertical support member 144. In any other configuration, the manipulation tab 142 is pressed downwardly toward the horizontal base 134, which in turn, compresses the torsion effect for the longitudinal extension bar 140 relative to the horizontal base 134. In this configuration, the fill limiter 16 may be slid forwardly or rearwardly along the shaft 14 or positioning groove 40 via the engagement between the first and second keels 130, 132 within the first pair of parallel channels 76, and/or the exterior edges 148 as positioned within the positioning channels 36 of the first and second handle members 28, 30 respectively. The fill limiter's 16 position relative to the positioning groove 40 may then be selected to a location which corresponds to a predetermined volume of liquid or drench within the cylinder 22. Upon alignment of the positioning locks 146 and locking channels 68, torsion effect between the longitudinal extension bar 140 and the horizontal base 134 will preferably be released and the positioning locks 146 will vertically engage the locking channels 68 adjacent to the positioning groove 40. The fill limiter 16 is thereby locked into a desired location where the stop ledge 136, rearward edge 149, or rearward surface 151 are located in a predetermined position for engagement to the vertical ledge 82 of the shaft 14. (FIGS. 2, 3, 4, 5, 6, 7, 8, and 8a)

As the grasping end 72 of the shaft 14 is rearwardly retracted, the vertical ledge 82 comes into contact with the stop ledge 136, rearward edge 149, or rearward surface 151 as locked into a desired location via the engagement between the positioning locks 146 within the locking channels 68. It should be noted that the vertical ledge 82 of the shaft 14 will always strike the stop ledge 136, rearward edge 149, or rearward surface 151, limiting the rearward retraction of the shaft 14 relative to the handle 12. (FIGS. 1, 2, 3, 4, 5, 6, 7 and 8)

The initial steps of assembly of the drench gun 10 include positioning of the shaft 14 within the rear aperture 34 and the nose aperture 46. The placement of the arcuate positioning tabs 114 onto the dispensing limiter pivot pin 64 may also occur to engage the dispensing limiter 18 to the first handle 28. Engaging the dispensing spring 60 to the dispensing spring pin 62, dispensing spring ledge 58 and to the spring channels 128 may also occur. Next, the positioning of the fill limiter 16 into straddling relationship with respect to the shaft 14 and positioning of an exterior edge 148 into a positioning channel 36 may occur. Engagement of the second handle member 30 to the first handle member 28 may then occur which results in the simultaneous engagement of the fill limiter 16 and the exterior edge 148 of the horizontal base 134 within the pair of positioning channels 36. The engagement of the second handle member 30 to the first handle member 28 also causes the pair of arcuate positioning tabs 114 to engage the pair of dispensing limiter pivot pins 64 and the dispensing spring 60 to engage the dispensing spring pin 62 and dispensing spring ledges 58. The second handle member 30 may then be secured to the first handle member 28 by the placement of screws and/or other affixation means within the screw tabs 52 and screw recesses. (FIG. 1)

Figure 12:
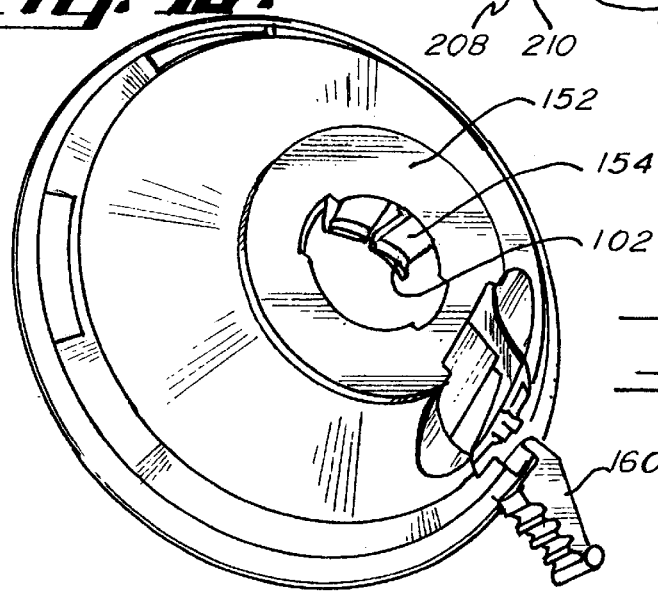
FIG. 12 is a detail isometric front view of the cone.

A cone 20 may then be engaged to the nose portion 44 of the handle 12. The cone 20, in general, includes a nose coupling 152 which includes fingers 154 and finger tabs 102. The cone 20 may also include a means for affixation 156 which may include one or more receiving members 158 and a first locking mechanism 160. (FIGS. 1, 11 and 12)

The nose coupling 152 is preferably adapted for receiving engagement of the nose 38 following affixation of the first and second handle members 28, 30 respectively, together. The nose coupling 152 assists in retention of the nose portion 44 of the first and second handle members 28, 30 together. The nose coupling 152 may include any desired number of forwardly extending fingers 154 with each finger 154 including a finger tab 102. The finger tabs 102 are preferably adapted for penetrating engagement into the nose slots 162 of the nose collar 104. Preferably, each finger tab 102 includes a ramped surface 164 which assists the fingers 154 to outwardly diverge during receiving engagement of the nose portion 44, and further assist in the penetrating engagement of the finger tabs 102 within the nose slots 162. The cone 20 may be disconnected from the nose 38 by the outward manipulation of the fingers 154 and separation of the finger tabs 102 from the nose slots 162, thereby permitting forward withdrawal of the cone 20 from the handle 12 and nose 38. (FIGS. 1, 11 and 12)

The means for affixation 156 is preferably used to couple the cone 20 to the cylinder 22. The means for affixation 156 may be clamps, interlocking members, mating teeth, threaded penetrating or receiving members, and/or any other affixation mechanism which releasably or permanently attaches the cone 20 to the cylinder 22. One suitable means for affixation 156 described herein is the use of receiving members 158 which are preferably adapted to couple with penetrating members 166 of the cylinder 22. A plurality of receiving members 158 may be spaced about the periphery of the cone 20 at the discretion of an individual. The receiving members 158 are preferably adjacent to receiving member recesses 168 which facilitate the positioning of the penetrating members 166 prior to engagement to the receiving members 158. To couple the cylinder 22 to the cone 20, the penetrating members 166 are preferably positioned within the receiving member recesses 168 whereupon the cylinder 22 may be rotated one-eighth of a turn, as indicated by arrow 170 to engage the receiving members 158. It should be noted that the receiving members 158 and penetrating members 166 may each include mating grooves, ledges, and/or channels which may be utilized to interconnect to each other for coupling of the cylinder 22 to the cone 20. (FIGS. 1, 11, 12 and 13)

The cone 20 may also include a first locking mechanism 160 which may include a grasping tab 172 which may be separated from the periphery of the cone 20 by a support member 174. The support member 174 provides flexibility and a limited range of outward motion for the first locking mechanism 160 relative to the periphery of the cone 20 to enable sufficient clearance for positioning of a penetrating member 166 within a receiving member recess 168 for engagement of the cylinder 22 to the cone 20. Following the rotation of the cylinder 22 in the direction of arrow 170, the first locking mechanism 160 may be released to return to a position adjacent to the periphery of the cone 20, whereon, the locking ledge 175 functions as a stop, prohibiting rotation of the cylinder 22 in a direction opposite to arrow 170 with respect to the cone 20. The first locking mechanism 160 thereby provides for the continued coupling of the cone 20 relative to the cylinder 22 until released by an individual. The first locking mechanism 160 also permits the cone 20 and cylinder 22 to be simultaneously removed from the handle 12 as a single unit. In this situation, the fingers 154 and finger tabs 102 are manipulated outwardly whereon the cone 20, and attached cylinder 22, may be removed from the handle 12 as a single unit. The first locking mechanism 160 prohibits the disengagement of the cylinder 22 from the cone 20. (FIGS. 1, 11, 12 and 13)

The interior of the cone 20 may also include a plurality of ribs 176 and support members 178 to assist in the provision of structural integrity and strength. The cone 20 may also include one or more apertures 179 which may be utilized to receive a portion of the finger guard 50 during coupling of the cone 20 to the handle 12. (FIGS. 11 and 12)

The cone 20 is preferably adapted to be replaceable for a different size cone 20 for use with a dispensing gun 10 of varying applications, such as with lubricants, and/or food. The coupling of a smaller or larger cone 20 to the nose 38 enhances the flexibility and utility of the dispensing gun 10 to an individual.

During assembly, a means for expansion 180 is preferably positioned between the cone 20 and the piston 24. The means for expansion 180 may preferably be a spring 182 which, in turn, may be a compression-type or otherwise at the preference of an individual. The means for expansion 180 may either be cylindrical and/or conical in shape, at the preference of an individual. The means for expansion is preferably positioned in surrounding engagement around the shaft 14. The spring 182 may be selected to have various sizes for provision of alternative tension compressions for utilization with different applications such as with syrup, lubricants, or thinner or thicker liquid solutions as desired by an individual. (FIG. 1)

The spring 182 may be cylindrical in shape where the diameter of the spring 182 may vary significantly at the preference of an individual. A cylindrical spring 182 may have a diameter dimension where one end of the spring 182 engages the interior of the cone 20 on the nose coupling 152. Alternatively, the spring 182 may have a larger diameter dimension where one end engages either the ribs 176 or support members 178 of the interior of the cone 20. The opposite end of the spring 182 preferably engages the piston 24. (FIG. 1)

In the preferred embodiment, the spring 182 may be conical in shape having a first end 184 having a larger diameter and a second end 186 having a smaller diameter. Preferably, the second end 186 is positioned for engagement to the nose coupling 152 and the first end 184 is preferably positioned for engagement to the piston 24. It should be noted that in this configuration a desired level of tension/compression is provided. (FIG. 1)

Alternatively, the first end 184 may be positioned for engagement to the ribs 176 and/or support members 178 and the second end 186 may be positioned for engagement to the piston 24 where an alternative tension/compression is provided for the dispensing gun 10 without replacement of the spring 182. It should also be noted that the ends of the spring 182 may be transposed and/or the spring 182 may be replaced to provide an individual with a desired level of tension/compression for use of the dispensing gun 10. The spring 182 is therefore intended to be reversible, removable, and/or replaceable. (FIG. 1)

Figure 18:
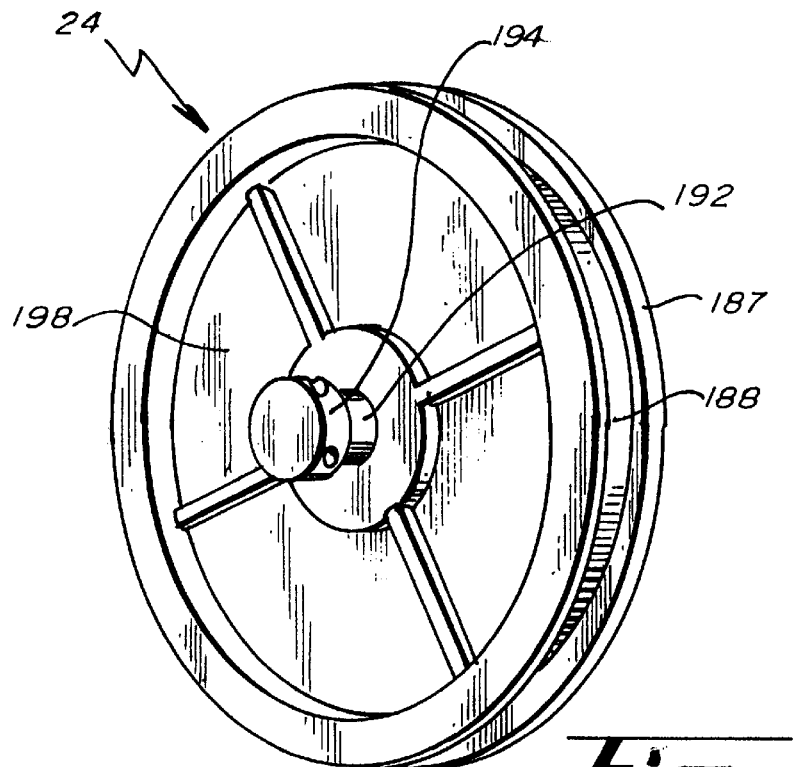
FIG. 18 is a detail isometric rear view of the retainer.
Figure 19:
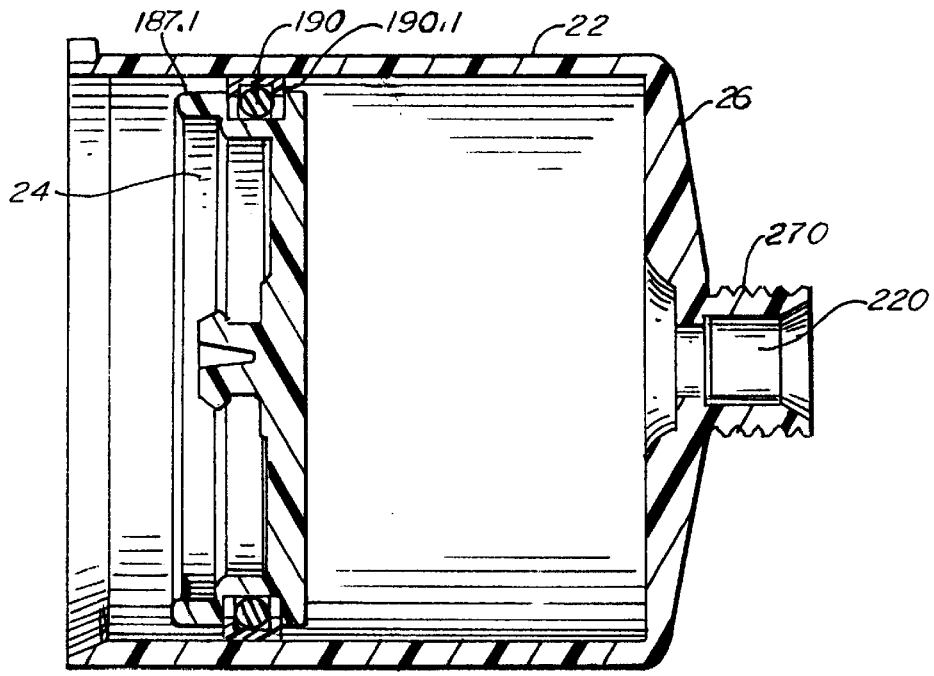
FIG. 19 is an alternative detail cross-sectional side view of the piston and cylinder.

Following the placement of the means for expansion 180 between the cone 20 and the piston end 74 of the shaft 14, the piston 24 may be engaged to the piston end 74. The piston 24 is preferably used to propel a desired volume of liquid and/or packet of liquid forwardly within the cylinder 22 for expulsion from the end cap 26 for introduction to an animal or other application. (FIGS. 1 and 18) The piston channel 188 may be centrally positioned with respect to the exterior wall 187 of the piston 24. Alternatively, the width dimension for the exterior wall 187 may be increased and the piston channel 188 may be offset with respect to the center as depicted in FIGS. 19 and 23. In addition, the exterior wall 187 may include a rearwardly extending ledge portion 187.1 which preferably enhances the structural strength and stability for the piston 24. (FIG. 19)

The piston 24 is preferably cylindrical in shape having a piston channel 188 which is preferably adapted for receipt of a piston O-ring 190 which provides a seal between the piston 24 and the interior wall of the cylinder 22. (FIGS. 1 and 18)

The piston 24 is also adapted to engage the piston end 74 of the shaft 14. The piston 24 may then be drawn rearwardly toward the handle 12 and cone 20 by retraction of the grasping end 72 of the shaft 14. The rearward retraction of the shaft 14 causes the piston 24 to compress the means for expansion 180 by reducing the space between the piston 24 and the nose coupling 152 and/or the cone 20. The piston 24 may move forwardly by the compression of the dispensing limiter 18 which releases the engagement between the dispensing barrier stop 118 and the notches 86, which, in turn, enables the means for expansion 180 to release tension, moving the piston 24 forwardly toward the end cap 26. (FIGS. 1, 2 and 3)

The piston 24 preferably includes an extension throat 192 and a piston tab 194. The piston tab 194 is preferably adapted for sliding engagement into the piston affixation notch 100. The extension throat 192 is preferably adapted for sliding engagement into the piston receiving slot 98 which includes a narrow portion 196 which, in turn, expands during receiving engagement of the extension throat 192.

Upon the positioning of the extension throat 192 completely within the piston receiving slot 98, the narrow portion 196 will contract around the extension throat 192 providing an affixation mechanism for the piston 24 relative to the piston end 74. (FIGS. 1 and 18) It should be noted that the piston tab 194 may be circular in shape as depicted in FIG. 18 or key-shaped as depicted in FIG. 23 at the preference of an individual. In addition, it should be noted that the extension throat 192 and piston receiving slot 198 may be of any shape as desired by an individual for mating engagement with either a circular or key-shaped piston tab 194. As depicted in FIG. 23, the piston tab 194 may also include a slot, channel, or aperture which may be adapted for receiving engagement of a projecting locking member integral to the grasping end 74 of the shaft 14 for enhanced affixation of the piston 24 to the shaft 14. It should be noted that the use of a circular piston tab 194 within a circular piston receiving slot 98 may permit the piston 24 to rotate about the shaft 14 during use of the dispensing gun 10.

The key-shaped piston tab 194 is preferably offset from center with respect to the piston 24 which is adapted to slidably engage a key hole shaped piston receiving slot 98 of the shaft 14. It should be noted that the use of key shapes for the piston tab 194 and piston receiving slot 98 prevent the circular rotation of the piston 24 relative to the shaft 14 and further minimizes wobble between the piston 24 and the interior of the cylinder 22 during use of the dispensing gun 10. The piston tab 194 is preferably sized for a tight friction fit within the piston receiving slot 98 which requires manipulation by an individual to separate the piston 24 from the shaft 14.

In an alternative embodiment, an O-ring 190 and a seal 190.1 may both be positioned in the piston channel 188. (FIG. 19) In this embodiment, the O-ring 190 functions as an energizer and the seal 190.1 functions to prohibit fluid passage from the cylinder 22 past the piston 24 during use of the dispensing gun 10. The seal 190.1 may be formed of any preferred material such as teflon, identified as the Turcon® Double Delta® as available from Busak and Shamban Midwest of Illinois. The use of the seal 190.1 enhances performance by minimizing breakaway start-up friction during use of the dispensing gun 10 while simultaneously minimizing sliding friction between the piston 24 and the cylinder 22. During use, the O-ring 190 provides an even outward force to the seal 190.1 which further enhances the use of a spring 182 having a reduced tension/compression rating. The use of the seal 190.1 further enhances the smooth flow of liquid as discharged through the end cap 26 during use of the dispensing gun 10.

The piston 24 is preferably interchangeable and is designed to accommodate use with various sized cylinders 22. As such, the piston 24 preferably includes the quick release feature of the extension throat 192 and piston tab 194 which further facilitate the removal of the piston 24 from the piston end 74 of the shaft 14. The quick release features of the piston 24 facilitate cleaning of the dispensing gun 10.

The piston 24 may also include a recessed portion 198 which is adjacent to the extension throat 192 and the piston tab 194. (FIGS. 1 and 18)

Figure 13:
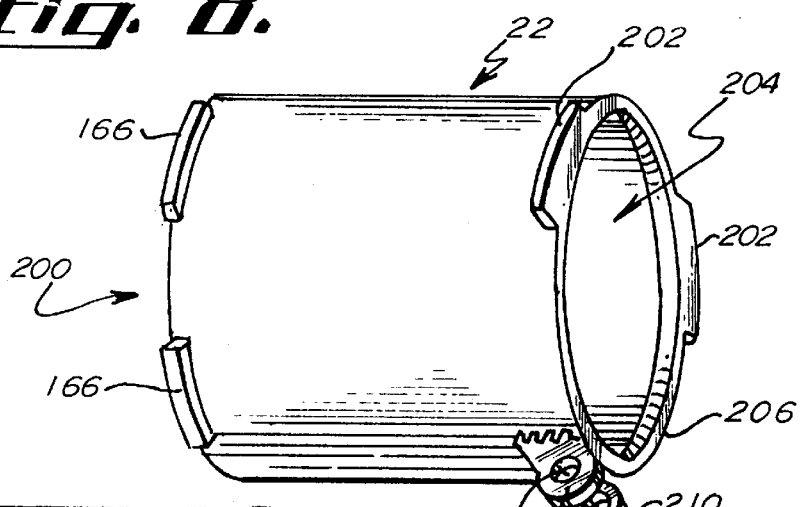
FIG. 13 is a detail isometric view of the cylinder.

The cylinder 22 generally includes an open end 200, a plurality of penetrating members 166, and plurality of penetrating retention members 202, an interior 204, a closeable end 206, and a mounting member 208. (FIGS. 1 and 13)

Following the engagement of the piston 24 to the piston end 74, the cylinder 22 may be engaged to the cone 20 via the coupling of the penetrating members 166 to the receiving members 158. The cylinder 22 is preferably interchangeable and quickly released from the cone 20 to accommodate cylinders 22 of different diameter and length dimensions for use within varying applications. As such, a cylinder 22 may have dimensions in length and diameter for confinement of liquids varying in volume between fifty cubic centimeters and three hundred fifty cubic centimeters or more. The cylinder 22 may also preferably confine premeasured individual bladders, packets, and/or containers of liquid at the discretion of an individual for use within the dispensing gun 10. It should be noted that the diameter dimension selected for the cylinder 22 is required to match the diameter dimension select for the cone 22 in order to enable coupling therewith. (FIGS. 1, 11, 12, 13 and 18)

The open end 200 of the cylinder 22 is preferably adapted for engagement to the cone 20. The closeable end 206 is preferably adapted to include an end cap 26. (FIG. 13)

The closeable end 206 preferably includes at least two penetrating retention members 202 adjacent to the periphery of the closeable end 206 of the cylinder 22. The mounting member 208 is also preferably attached to or integral with the cylinder 22 proximate to the closeable end 206. (FIG. 13)

The mounting member 208 may be formed of a pair of mounting tabs 210, where each mounting tab 210 may include a centrally positioned aperture 212 therethrough. The mounting tabs 210 preferably enable and provide for pivotal engagement of the end cap 26 relative to the closeable end 206 of the cylinder 22. The penetrating retention members 202 preferably provide the mechanism for engagement to a second locking mechanism 214 which is preferably used to seal and secure the end cap 26 to the closeable end 206 of the cylinder 22. Alternatively, the end cap 26 may be threadably engaged and/or screwed upon the closeable end 206 at the discretion of an individual. (FIGS. 1, 13, 14 and 15) Alternatively, the cylinder 22 and end cap 26 may be an integral one-piece unit. (FIG. 19) In this embodiment, the end cap 26 fixedly encloses the closable end 206 of the cylinder 22.

Figure 20:
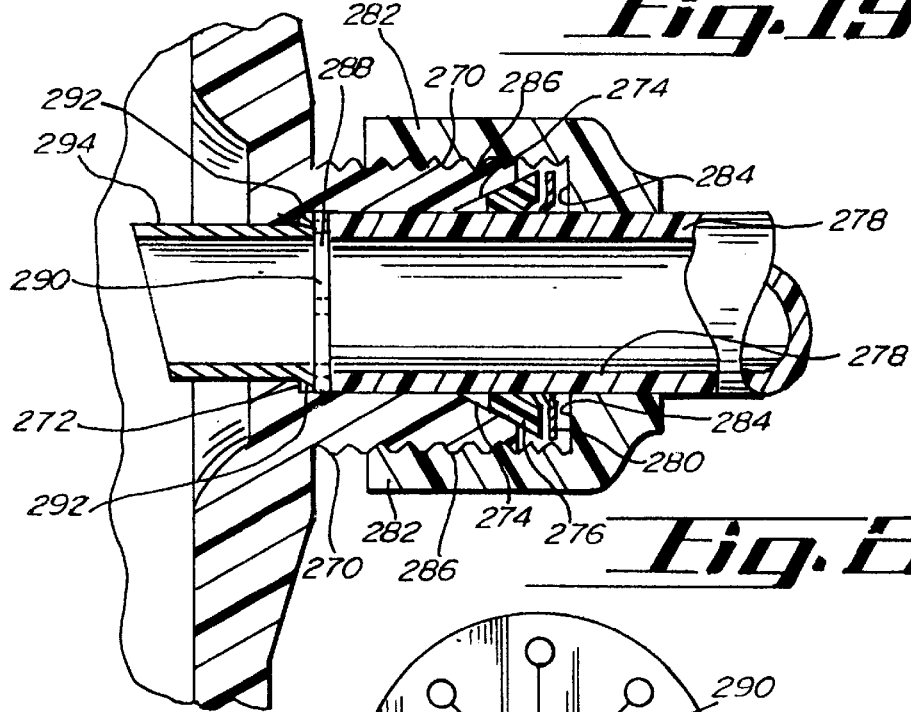
FIG. 20 is an alternative detail cross-sectional side view of the end cap outlet.

The end cap 26, in general, includes a piercing member 216, an outlet aperture 218, an outlet 220, a mounting fixture 224, and a sealing ledge 234. (FIGS. 14 and 15) In an alternative embodiment, the end cap 26 may include an outlet 220 having a threaded exterior 270, an interior positioning ledge 272, and an inclined throat surface 274. The inclined throat surface 274 is preferably adapted for engagement to a cone washer 276 which is preferably positioned between, and engaged to, the inclined throat surface 274 and a discharge tube 278. The discharge tube 278 may preferably be formed of nylon, steel, rubber, or copper material at the discretion of an individual, and is preferably used for introduction into an animal's mouth during discharge of drench from the dispensing gun 10. A grip ring 280 may also be positioned for surrounding the exterior of the discharge tube 278 and positioned adjacent to the cone washer 276. (FIGS. 19 and 20)

A tail piece nut 282 having an engagement ledge 284 and a threaded grasping surface 286 may be engaged to the outlet 220. The threaded grasping surface 286 may preferably be adapted for mating engagement to the threaded exterior 270 of the outlet 220 of the end cap 26. The engagement ledge 284 is preferably adapted to engage the gripping ring 280 and/or cone washer 276 for establishment of a seal between the discharge tube 278 and the end cap 26. (FIGS. 19 and 20)

Figure 22:
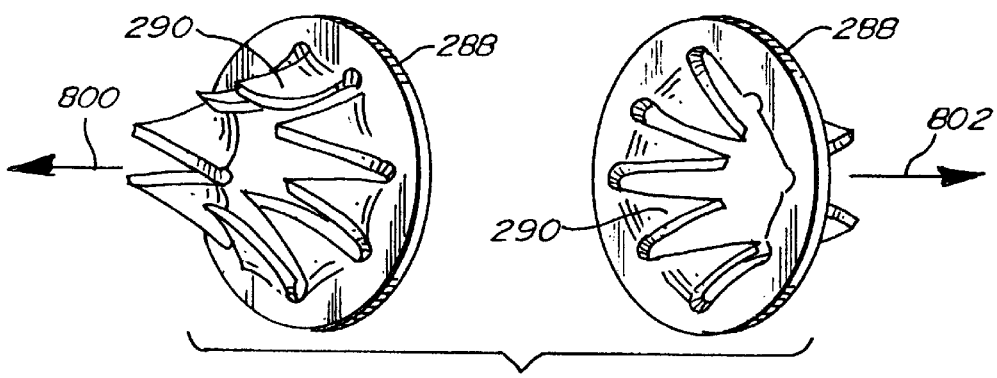
FIG. 22 is a detail environmental view of the flow control wafer.
Figure 21:
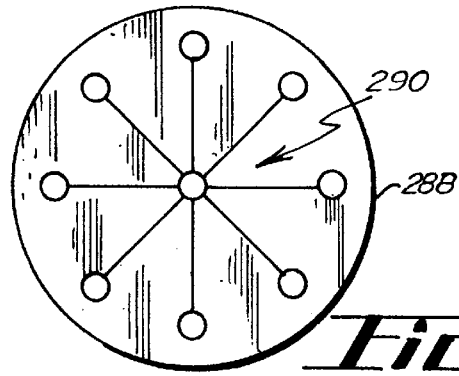
FIG. 21 is a detail end view of the flow control wafer.

A flow control wafer 288 may be positioned between the end of the discharge tube 278 and the interior positioning ledge 272 of the outlet 220 of the end cap 26. The flow control wafer 288 may be formed of rubber or any other suitable and resiliently pliable material at the discretion of an individual. The flow control wafer 288 may include a plurality of finger segments 290 which may be formed by cutting of the material of the flow control wafer 288. The finger segments 290 preferably are of equal size and extend radially outwardly from the center of the flow control wafer 288. The finger segments 290 preferably may move in either an outward or inward direction as indicated by arrows 802 and 800 respectively, with respect to the outlet 220, dependent upon the discharge from, or filling of, the cylinder 22 with liquid and/or drench. The finger segments 290 preferably have a resiliently pliable memory to return the plurality of finger segments 290 to a substantially planar configuration during periods where the fluid flow through the dispensing gun 10 is terminated. The finger segments 290 preferably assist in the prevention of air bubbles from traveling through the discharge tube 278 through the outlet 220 and into the cylinder 22, which, in turn, will cause liquid to drip from the dispensing gun 10. The finger segments 290 thereby assist in the reduction of waste and drip from the dispensing gun 10 during periods of non-use between animal introductions. In addition, the resiliently flexible nature of the finger segments 290 further assists in the prevention of flow of liquid from the cylinder 22 through the outlet 220 and into the discharge tube 278 when the dispensing limiter 18 is not being engaged by an individual. (FIGS. 21 and 22)

In an alternative embodiment, a cutter ring 292 may be positioned between the interior positioning ledge 272 and the flow control wafer 288. The cutter ring 292 preferably includes a plurality of penetrating shanks 294 which may be utilized to pierce and/or rupture a bladder of liquid and/or drench as positioned within the cylinder 22. The cutter ring 292 may be utilized individually with or without a flow control wafer 288 and is preferably held in fixed position between the interior positioning ledge 272 and the end of the discharge tube 278 by the engagement of the threaded grasping surface 286 of the tail piece nut 282 to the threaded exterior 270 of the outlet 220 of the end cap 26. The cutter ring 292 may preferably be formed of stainless steel metal material. Alternatively, any other material such as rigid plastics or metals may be used to form the cutter ring 292 at the preference of an individual provided that the essential functions, features, and attributes described herein are not sacrificed.

The end cap 26 may preferably be pivotally mounted to the closeable end 206 of the cylinder 22 via the engagement between the mounting fixture 224 and the mounting member 208. The mounting fixture 224 preferably includes a centrally positioned aperture 226 therethrough. The apertures 212 and 226 are preferably aligned and are adapted for receiving engagement of a pivot pin 240 which enables the end cap 226 to pivot relative to the closeable end 206. The mounting fixture 224 preferably extends from the end cap 26 via a support extension 228 which provides the necessary clearance for positioning of the sealing ledge 234 completely within the closeable end 206 to facilitate and preferably achieve sealing of the cylinder 22 during use of the dispensing gun 10. (FIGS. 1, 13, 14 and 15)

The sealing ledge 234 is preferably adjacent to an O-ring groove 236 which may preferably be adapted for receiving engagement of an O-ring 222 which may be utilized to obtain a seal of the end cap 26 relative to the cylinder 22. The sealing ledge 234 is also proximate to a lip 232 which defines the periphery of the end cap 26 and preferably overlaps the closeable end 206. The lip 232 preferably includes a sufficient width dimension to extend outwardly from the closeable end 206 around the entire periphery or circumference of the end cap 26. It should be noted that when the end cap 26 is positioned into sealing engagement with the closeable end 206, then the sealing ledge 234, O-ring groove 236, and O-ring 222 are completely within the interior 204 of the cylinder 22 and that the lip 232 is in engagement with the closeable end 206. (FIGS. 1, 13, 14 and 15)

The end cap 26 may preferably include a piercing member 216 which is preferably adapted for positioning within the interior 204 of the cylinder 22 during use of the dispensing gun 10. The piercing member 216 is preferably centrally positioned within a central crater 238 which, in turn, is centrally positioned with respect to the interior surface of the end cap 26. The piercing member 216 may also preferably include a plurality of apertures to permit fluid flow passage therethrough. (FIGS. 13, 14 and 15)

In operation, during use of a bladder, packet, or container of liquid, the compression of the dispensing limiter 18 releases the means for expansion 180 which, in turn, assist the shaft 14 and piston 24 to actuate and/or move toward the end cap 26. Any bladder, packet, and/or container of liquid disposed within the cylinder 22 will therefore be compressed against the piercing member 26 whereupon rupturing of the bladder, packet, and/or container may occur for the expulsion of liquid through the end cap 26.

An outlet 220, having a centrally disposed outlet aperture 218 is preferably in fluid-flow communication with the piercing member 216 to permit fluid passage from the interior 204 of the cylinder 22 through the outlet 220 and outlet aperture 218. It should be noted that the piercing member 216, having the plurality of apertures, may also preferably permit fluid passage through the outlet 220 and outlet aperture 218 when fluid is disposed directly within the interior 204 of the cylinder 22 without the use of bladders, packets, and/or containers Of liquid. (FIGS. 13, 14 and 15)

The outlet 220 may include a plurality of regularly spaced grooves and/or ribs at the preference of an individual to assist in the retention of an application hose engaged to the outlet 220. The application hose may be used for insertion into an animal's mouth to facilitate the introduction of drench and/or liquid during use of the dispensing gun 10. (FIGS. 14 and 15)

The end cap 26 may also include a raised surface tab 242 which is preferably adapted for grasping by an individual during the pivoting of the end cap 26 into closing and/or sealing relationship with respect to the closeable end 206 of the cylinder 22. It should be noted that the sealing of the end cap 26 relative to the cylinder 22 enables the cylinder 22 to be filled with liquid by the placement of the outlet 220 or a hose connected to the outlet 220 into a bulk container of liquid and the subsequent retraction of the grasping ends 72 of the shaft 14 which, through suction, fills the interior 204 of the cylinder 22 with liquid. The volume of liquid to be drawn into the interior 204 of the cylinder 22 may be regulated by the positioning of the fill limiter 16 as earlier described. (FIGS. 13, 14 and 15)

It should also be noted that the end cap 26 may also include a plurality of structural supports 230 at the discretion of an individual and that sealing ledge 234 is sized to exactly fit into sealing engagement within the interior 204 of the closeable end 206 of the cylinder 22 and that the O-ring 222 assists in the acquisition of a seal therebetween which, in turn, facilitates the suction of liquid within the interior 204 of the cylinder 22 during use of the dispensing gun 10. In addition, the sealing engagement between the end cap 26 and the closeable end 206 forces liquid to exit the cylinder through the outlet 220 thereby minimizing waste of liquid to an individual. (FIGS. 13, 14 and 15)

Figure 17:
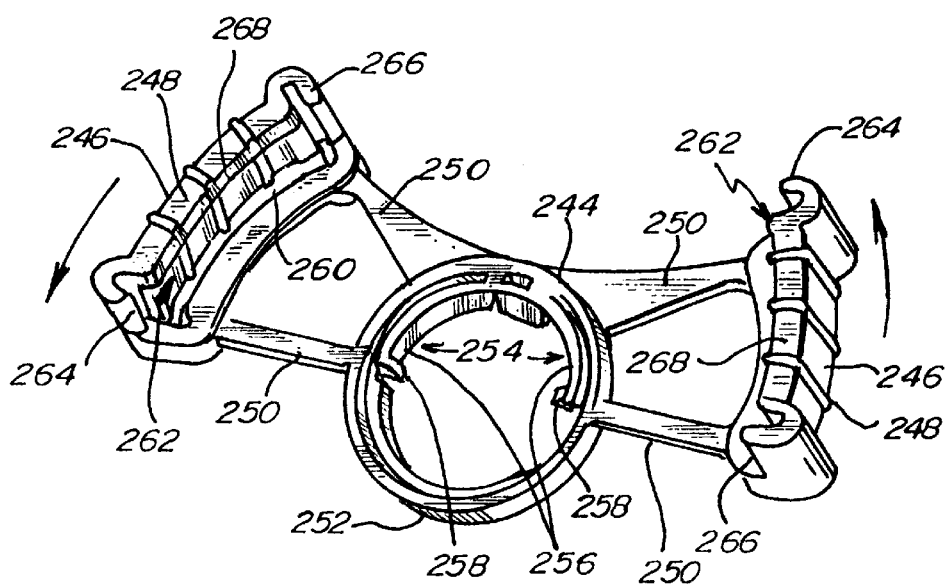
FIG. 17 is an isometric detail view of the retainer.

The second locking mechanism 214 preferably prevents the involuntary or undesirable separation of the end cap 26 from the cylinder 22. The second locking mechanism 214 may be threaded members, clasps, or any other affixation means as preferred by an individual. (FIGS. 16 and 17)

The second locking mechanism 214 may be formed of a retainer 244. The retainer 244 preferably includes a pair of retainer handles 246 where each retainer handle 246 may include raised ribs 248 to facilitate grasping by an individual. The retainer 244 may also include a plurality of support arms 250 which are preferably connected to a central collar 252. The central collar 252 is preferably adapted for receiving engagement of the outlet 220 of the end cap 26. The support arms 250 preferably are of sufficient strength and durability to securely affix the central collar 252 to the retainer handles 246 without fracture or failure during use of the dispensing gun 10. (FIGS. 1, 16 an 17)

The central collar 252 may include a third locking mechanism referred to in general by the numeral 254. The third locking mechanism 254 may include a pair of flexible lock arms 256 where each lock arm 256 may include a locking tab 258. The locking arms 256 and locking tabs 258 are preferably adapted to engage and grasp the outlet 220. The outlet 220 is preferably inserted for penetrating engagement within the central collar 252 whereupon the lock arms 256 may flex outwardly as the outlet 220 is inserted further within the central collar 252, whereupon the locking tabs 258 may engage one of the plurality of ribs of the outlet 220 preventing involuntary separation of the end cap 26 from the retainer 244. (FIGS. 1, 16 and 17)

Each of the retainer handles 246 preferably has a receiving retainer slot 260 which is preferably adapted for receiving and locking engagement to a penetrating retention member 202 of the cylinder 22. Each receiving retention slot 260 is preferably accessible through an access ledge opening 262 which is preferably defined by an access ledge 264. The access ledge opening 262 is defined by the shorter dimension and size of the access ledge 264 relative to the termination ledge 266 which, in turn, functions as a stop, limiting the further engagement of the penetrating retention members 202 within the receiving retainer slot 260. Each receiving retainer slot 260 preferably also includes an overlap member 268 which further facilitates the engagement of the penetrating retention members 202 within the receiving retainer slot 260 preventing involuntary lateral separation therefrom. (FIGS. 1, 13, 16 and 17)

The retainer 244 may be engaged to the penetrating retention member 202 of the cylinder 22 following the positioning of the end cap 26 into sealing engagement with the cylinder 22. The central collar 252 may then be positioned for receiving penetrating engagement of the outlet 220. The retainer 244 may then be adjustably rotated for positioning of the penetrating retention members 202 adjacent to the access ledge openings 262. The retainer handles 246 may then be rotated one-eighth of a turn for insertion of the penetrating retention members 202 within the receiving retainer slots 260. Rotation of the retainer 244 may continue until the penetrating retention members 202 engage the termination ledges 266 whereon rotation of the retainer 244 stops. The overlap members 268 preferably prevent involuntary separation of the penetrating retention members 202 from the receiving retention slots 260, effectively performing the function of the third locking mechanism for the end cap 26 into sealing engagement with the cylinder 22. (FIGS. 1, 13, 16 and 17)

It should be noted that a cavity is formed between the piston 24 and the end cap 26 upon retraction of the shaft 14 within the interior 204 of the cylinder 22. This cavity is preferably adapted for receipt of a bladder, cartridge, and/or premeasured container of liquid. The bladder, packet, and/or container of liquid is positioned within the interior 204 of the cylinder 22 prior to the utilization of the retainer 244 to seal the end cap 26 to the cylinder 22. Alternatively, the end cap 26 may be sealed with respect to the cylinder 22 for filling of the interior 204 of the cylinder 22 from a bulk container of liquid via the retraction of the shaft 14 and the simultaneously positioning of the outlet 220 within the bulk container of liquid.

The dispensing gun 10 is preferably spring assisted via the means for expansion 180 which preferably minimizes fatigue to an individual's hands and/or arms during use. In addition, the dispensing gun 10 is preferably adapted for one-handed use by an individual where the person's free hand may be used to control the head and/or neck of an animal during the introduction of drench and/or liquid. Further, the dispensing gun 10 preferably regulates the rate of liquid to be dispensed to an animal, which further minimizes coughing and/or rejection of drench which minimizes waste to an individual.

The present invention may be embodied in other specific forms without departing from the spirit or essential attributes thereof, therefore, the illustrated embodiment should be considered in all respects as illustrative and not restrictive, reference being made to the appended claims rather than to the foregoing description to indicate the scope of the invention.

What is claimed:

1. A dispensing gun comprising:
   (a) a handle having a hand grasping portion and a nose, said hand grasping portion comprising a fill limiter;
   (b) a shaft having a grasping end and a piston end, said shaft being engaged to said handle proximate to said nose;
   (c) a cylinder having an interior engaged to said handle proximate to said nose;
   (d) a piston engaged to said piston end, said piston disposed within said interior of said cylinder; and
   (e) a means for expansion disposed within said interior of said cylinder, said means for expanding being positioned between said piston and said handle.

2. The dispensing gun of claim 1, the hand grasping portion further comprising a first handle member engaged to a second handle member defining an internal cavity and said nose, said nose comprising a nose aperture therethrough, said shaft positioned through said nose aperture.

3. The dispensing gun of claim 2, said hand grasping portion further comprising a channel, said fill limiter slidably positioned within said channel.

4. The dispensing gun of claim 3, said hand grasping portion further comprising a dispensing limiter pivotally engaged to said hand grasping portion.

5. The dispensing gun of claim 4, said shaft further comprising a ledge and a plurality of notches, said dispensing limiter adapted for engagement to said notches.

6. The dispensing gun of claim 5, further comprising a cone having a nose coupling engaged to said nose, and a receiving member.

7. The dispensing gun of claim 6, said cylinder further comprising:

(a) an open end having an engagement portion adapted to releasably affix said cylinder to said receiving member; and (b) an end cap opposite to said open end for sealing of said cylinder, said end cap further having an outlet in communication with said cylinder.

8. The dispensing gun of claim 7, said means for expansion comprising a spring.

9. The dispensing gun of claim 7, wherein said spring is conical in shape, having a first end having a large diameter and a second end having a small diameter where said first end may be positioned proximate to either said nose or to said piston.

10. A dispensing gun comprising:
(a) a handle comprising:
(i) a dispensing limiter;
(ii) a fill limiter; and
(iii) a nose portion;
(b) a shaft comprising a grasping end and a piston end, said shaft being engaged to said dispensing limiter;
(c) a cone engaged to said nose portion;
(d) a cylinder having an interior engaged to said cone;
(e) a piston engaged to said piston end, said piston disposed within said interior of said cylinder; and
(f) a spring disposed inside said cylinder, said spring being engaged to said piston and positioned between said piston and said handle.

11. The dispensing gun of claim 10, said handle further comprising a first handle member engaged to a second handle member defining an internal cavity, said nose portion further comprising a nose aperture therethrough.

12. The dispensing gun of claim 11, said handle further comprising a channel traversing said first handle member and said second handle member, said fill limiter slidably positioned within said channel.

13. The dispensing gun of claim 12, wherein said dispensing limiter is pivotally engaged to either said first handle member or to said second handle member, a portion of said dispensing limiter extending at least partially into said internal cavity.

14. The dispensing gun of claim 13, further comprising a dispensing spring engaged to said handle and to said dispensing limiter.

15. The dispensing gun of claim 14, said shaft further comprising a ledge adapted for engagement to said fill limiter, and a plurality of notches adapted for engagement to said dispensing limiter, said shaft passing through said nose aperture.

16. The dispensing gun of claim 15, said cone further comprising a means for affixation for engagement to said cylinder.

17. The dispensing gun of claim 16, said cylinder further comprising:
(a) an open end having an engagement portion adapted to releasably affix said cylinder to said means for affixation; and
(b) an end cap opposite to said open end for sealing of said cylinder, said end cap further having an outlet in communication with said cylinder.

18. The dispensing gun of claim 17, wherein said spring is conical in shape having a first end having a large diameter and a second end having a small diameter.

19. The dispensing gun of claim 18, wherein said first end of said spring may be positioned proximate to either said nose portion or to said piston.

20. A dispensing gun comprising:
(a) a handle comprising:
(i) a first handle engaged to a second handle defining an internal cavity and a nose, said nose having a nose aperture;
(ii) a channel traversing said first handle and said second handle;
(iii) a fill limiter slidably positioned within said channel;
(iv) a dispensing limiter pivotally engaged to said first handle or to said second handle, a portion of said dispensing limiter extending at least partially within said internal cavity; and
(v) a dispenser spring engaged to said handle and to said dispensing limiter;
(b) a shaft comprising:
(vi) a grasping end and a piston end, said shaft being retractably positioned within said internal cavity and said nose aperture;
(vii) a ledge adapted for engagement to said fill limiter; and
(viii) a plurality of notches adapted for engagement to said dispensing limiter;
(c) a cone comprising:
(ix) a nose coupling adapted to engage said nose;
(x) a receiving member; and
(xi) a first locking mechanism;
(d) a cylinder having an interior comprising:
(xii) an open end having an engagement portion adapted to engage said first locking mechanism to releasably affix said cylinder to said receiving member; and
(xiii) an end cap opposite to said open end for sealing of said cylinder, said end cap having an outlet in communication with said outlet cylinder;
(e) a piston releasably engaged to said piston end, said piston being disposed within said interior of said cylinder; and
(f) a means for expansion disposed within said interior of said cylinder, said means for expansion being positioned between said piston and said nose coupling.

21. The dispensing gun of claim 20, said means for expansion comprising a spring.

22. The dispensing gun of claim 21, wherein said spring is conical in shape having a first end having a large diameter and a second end having a small diameter.

23. The dispensing gun of claim 22, wherein said first end of said spring may be positioned proximate to said nose or to said piston.

* * * * *